United States Patent [19]

Burrell et al.

[11] Patent Number: 5,695,857
[45] Date of Patent: Dec. 9, 1997

[54] ACTIVELY STERILE SURFACES

[75] Inventors: Robert Edward Burrell, Sherwood Park; Aron Marcus Rosenfeld; Timothy J. N. Smith, both of Kingston, all of Canada

[73] Assignee: Westaim Technologies Inc., Alberta, Canada

[21] Appl. No.: 78,223

[22] PCT Filed: Dec. 23, 1991

[86] PCT No.: PCT/CA91/00453

§ 371 Date: Aug. 23, 1993

§ 102(e) Date: Aug. 23, 1993

[87] PCT Pub. No.: WO92/11043

PCT Pub. Date: Jul. 9, 1992

[30] Foreign Application Priority Data

Dec. 24, 1990 [CA] Canada ................ 2033107

[51] Int. Cl.⁶ ................................................ B32B 3/00
[52] U.S. Cl. ................ 428/209; 428/411.1; 428/434; 428/457; 428/458; 428/461; 428/689; 604/905

[58] Field of Search ............... 604/265, 905; 428/461, 434, 457, 458, 689, 209, 304.4, 411.1

[56] References Cited

U.S. PATENT DOCUMENTS

| 4,476,590 | 10/1984 | Scales et al. ............... 3/1.91 |
| 4,615,705 | 10/1986 | Scales et al. ............... 623/11 |
| 4,886,505 | 12/1989 | Haynes et al. ............. 604/265 |
| 5,320,908 | 6/1994 | Sodervall et al. ........... 428/461 |

FOREIGN PATENT DOCUMENTS 0206024A 12/1986 WIPO.

*Primary Examiner*—William Krynski
*Attorney, Agent, or Firm*—Cooper & Dunham LLP

[57] ABSTRACT

An actively antimicrobial surface for a substrate and for use in a biologically dynamic environment, such as for treating and preventing microbial infections, comprises a film consisting of at least an antimicrobial element and another electrochemically nobler element and which forms multitudinous galvanic cells with electrolyte containing biological fluids, such as body fluids from wounds, etc., for releasing the antimicrobial element at the surface.

21 Claims, 2 Drawing Sheets

ETCHING

SHADOW DEPOSITION 5,695,857

ACTIVELY STERILE SURFACES

TECHNICAL FIELD

This invention relates to actively antimicrobial surfaces useful in avoiding, preventing and treating bacterial, fungal and microbial infections generally by releasing substances which are active in suppressing such organisms.

It has been appreciated for some time that certain ions and compounds are very effective antimicrobials for treating and/or killing bacterial and fungal entities. Metallic silver and silver salts have been used to inhibit growth of microorganisms on fresh wounds and the like. Silver nitrates have been commonly used as bactericidal agents.

A problem with the in vivo use of metal for metal ion therapy in preventing and treating infections is that the results have never been too spectacular. This is primarily due to the very low concentration of active metal ions and, in most situations, the rapid decline in the presence of metal ions when derived from salt solutions as administered to the infected area.

BACKGROUND ART

Considerable research work has been conducted in the field of silver metal treatment of bacterial infections. A variety of silver coated nylon cloths and fibers have been investigated, such as disclosed in *Antimicrobial Agents and Chemotherapy*, March 1983, pp. 356–359, Deitch et al, "Silver-Nylon: a New Antimicrobial Agent"; *Antimicrobial Agents and Chemotherapy*, January 1987, pp. 93–99, MacKeen et al, "Silver-Coated Nylon Fiber as an Antibacterial Agent"; and in *The Journal of Trauma*, Volume 27, No. 3, Deitch et al, "Silver Nylon Cloth: In vitro and in vivo Evaluation of Antimicrobial Activity".

In the last noted reference, the use of a weak direct current to increase the rate of release of silver ions was investigated to determine the impact of the increased presence of silver ions. This aspect has been further investigated by several groups as reported in *Antimicrobial Agents and Chemotherapy*, February 1976, pp. 357–358, Berger et al, "Electrically Generated Silver Ions: Quantitative Effects on Bacterial and Mammalian Cells"; *Antimicrobial Agents and Chemotherapy*, November 1976, pp. 856–860, Berger et al, "Antifungal Properties of Electrically Generated Metallic Ions"; *American Journal of Veterinary Research*, Volume 41, No. 6, pp. 964–966, Colmano et al, "Activation of Antibacterial Silver Coatings on Surgical Implants by Direct Current: Preliminary Studies in Rabbits"; and *Plastic and Reconstructive Surgery*, Volume 77, No. 3, March 1986, Falcone et al, "Inhibitory Effects of Electrically Activated Silver Material on Cutaneous Wound Bacteria".

The technique of applying a current to a silver coated dressing or purifying devices or medical devices are also disclosed in U.S. Pat. Nos. 4,291,125; 4,411,648 and published U.K. Patent Application 2,189,677. It is thus apparent that considerable work has been conducted in the field of supplying silver ions in the area of infection or microbial contamination to control and eliminate microbial growth. This concept has been extrapolated further into the field of water treatment, such as disclosed in U.S. Pat. No. 4,407,865 where sand or diatomaceous earth is coated with metallic silver to provide a sterilizing effect as the contaminated waters flow over the filtered material.

It is apparent that sources of silver ions for instance would be particularly useful in surgical and other types of wound dressings. This aspect has been investigated and reported in U.S. Pat. No. 3,800,792, Canadian Patent 1,212,879 and published U.K. Patent Application 2,134,791. Metallic silver is incorporated into the dressing in one form or another and through dissolution silver ions are released into the treated area. U.K. Patent Application 2,134,791 discloses that composites containing various metals, such as silver, gold, palladium, platinum and tin are useful in surgical dressings, where the preferred metal is silver. It is postulated that the slow release of silver ions is facilitated by a galvanic interaction with the moss; i.e., substrate, of the dressing with added metallic or nonmetallic compounds. However, this patent is silent on how galvanic interaction is developed and directed towards slow release of silver ions in this moss based dressing composition.

European Patent Application 0206024 discloses use of very smooth coatings of various metal combinations on medical devices, such as catheters to provide some antimicrobial activity when the devices are in contact with body fluids.

U.S. Pat. No. 4,418,686 and published U.K. Patent Application 2,194,155A are directed to an implant active in releasing silver ions to treat a bacterial infection. In U.S. Pat. No. 4,418,686, the implant consists of a plurality of spaced-apart metallic bands on a plastic insert where the surfaces of the bands consist of alternate materials, such as silver and gold. The presence of the silver and gold metals in the presence of body fluids results in a galvanic action which is intended to release or liberate silver ions. The implant is of a coiled construction and has metallic bands of considerable size. Such obtained macroscopic galvanic action is not effective, or suitable for most surgical dressings. U.S. Pat. No. 4,252,525 discloses a dental implant where spaced-apart bands of silver and gold are vacuum deposited onto the body of the implant. In addition to these metals, other suitable substances include aluminum, copper, zinc, alloys such as silver-zinc-allantoinate, and silver sufadiazine, for release of metal ions in providing bactericidal and germicidal action. Other types of implants, which have been treated with silver ions, include catheters which are marketed by Baxter Travenol Laboratories under the trade mark AgX.

The prior techniques involving the use of metal ions in treating microbial infections do not provide a sustained enhanced release of antimicrobial substances. Most existing devices are for short-term applications or suffer from the drawback of very slow release of material. The elements of interest are in fact among the most stable elements. They do not readily dissolve at significant rates on their own, and when in contact with most other metals, will cause such others preferential release. Even when in contact with nobler metals, the differences on the electrochemical scale are quite small that galvanic action occurring over macroscopic areas of contact does not significantly enhance the release of ions to the level needed.

It is appreciated that the release of metal ions may be expedited by the application of external electric current. However, in many applications, such as in normal bandages or implants, this is practically impossible.

A variety of materials are used every day in treating or preventing infections in humans, animals and the like. For example, catheters, sutures, surgical gloves, implants, bandages, diapers, diaper liners, dressings, small adhesive dressings, sanitary napkins and insoles are just a few. Normally, bandages are used as a barrier to airborne pathogenic organisms infecting a cut or wound. However, once infection occurs, the bandage is no longer of any benefit. If the bandage were provided with a broad spectrum antimicrobial agent, on the portion of the bandage which is in contact with the wound and surrounding skin, the bandage becomes an actively rather than a passively antimicrobial surface or microbial barrier. Catheters, implants, bandages, dressings and other materials, such as above, are used extensively every day by millions of people. As a result, any form of antimicrobial material incorporated into these types of devices must be safe for general unsupervised use, should avoid selection of resistant strains, and should be cost effective. Furthermore, the materials may have to retain their flexibility such as with bandages so as to be readily usable.

It is an object of this disclosure to meet the difficulties encountered in the prior art and to make available both safe and economical actively antimicrobial surface structures and their method of manufacture.

Catheters, implants, bandages, diapers, diaper liners, dressings, and the like can be readily coated with thin films of active elements which, when in contact with body fluids, release substances and ions which stop the growth of or kill various types of microorganisms. As here described, there is no requirement to apply any outside electric current to maintain sustained levels of ion release to treat the infected area.

DISCLOSURE OF INVENTION

In accordance with a first aspect of the invention there is provided on a substrate for use with biological fluids, an actively antimicrobial surface film, comprising;

at least a pair of superimposed layers on the substrate, the layers of each pair being in electrical contact with each other, one of the layers in each pair being formed from a first element, the other of the layers in each pair being formed from a second element different from the first element, the second element being electrochemically nobler than the first element, at least the first element being an antimicrobially active metal element, each of the layers not in contact with the substrate being substantially discontinuous such that the layer below is exposed, whereby the first element releases ions of the antimicrobially active metal element when a biological fluid is brought into contact with the actively antimicrobial surface film.

In accordance with a second aspect of the invention there is provided a process for the production of an actively antimicrobial surface film on a substrate for use with electrolytes containing biological fluids, which comprises the steps of;

forming a first layer comprising one of a first element or a second element on a surface of the substrate;

forming a second layer comprising the other of the first element or the second element on the first layer; and texturing at least the second layer, and optionally the first layer to expose the first layer;

wherein at least the first element is an antimicrobially active metal element, the second element being different from, and electrochemically nobler than the first element, and the first and second elements in the first and second layers being in electrical contact with each other, and whereby when a biological fluid is brought into contact with the actively antimicrobial surface film, both the first and second layers are contacted and the first element releases ions of the antimicrobially active metal element.

In accordance with a third aspect of the invention there is provided on a substrate for use in a biologically dynamic environment, an actively antimicrobial surface characterized in;

an alloy of elements, one of said elements being antimicrobially active and another of said elements being nobler in the electrochemical series than said one element, both said elements being mutually insoluble in solid solution in said alloy, said alloy thereby releasing ions of said one element when said surface is contacted by electrolyte containing biological fluid.

In accordance with a fourth aspect of the invention there is provided a process for the production of an actively antimicrobial surface film on a substrate for use in a biological environment, which comprises the steps of, forming a first layer comprising a first element on a surface of said substrate;

texturing said first layer, shadow depositing a second element on the said first layer to provide areas of said first layer covered by said second element and areas not covered by said second element, at least one of the first and second elements being antimicrobally active and the other element being electrochemically nobler than said one element, said one element being ionically soluble in electrolytic biological fluid brought into contact with said layer.

A variety of ions are active in treating various types of microbial infections or acting as antimicrobials. Some preferred active element ions which have antimicrobial activity are those of platinum, gold, silver, copper, zinc, tin, antimony, and bismuth.

The antimicrobial films here described provide, in the presence of an electrolyte, such as provided by body or other biological fluid, an unexpected high reactivity of both the active element and the more noble element, which are released as ions (including ions of the nobler element in some instances, not merely in atomic form) to provide high antimicrobial efficacy.

All the mechanisms of ion release from the films are not yet fully understood, but it is thought that the large surface for galvanic action results, in the presence of electrolyte, in the high reactivity of the substances which are obtained.

Both micro-galvanic action and non-galvanic action will contribute to substance release from the film. The element or metal released by galvanic action, namely the one that is less noble on the electrochemical scale, is referred to herein as the "active element". Both the active element and the nobler element are released and contribute to the antimicrobial activity. The enhanced release of the nobler substances or ions from the actively antimicrobial surface film is referred to herein as occurring by "non-galvanic action".

Various embodiments of the invention are exemplified. Although discrete thin layers of the appropriate active elements or metals and more noble elements may be used, it is also evident that alloys, of the various active elements with the nobler elements also work well. The alloy can be of one active element with one nobler element or an alloy of several elements, compounds or metals with at least one or more nobler element.

Alloys where the active element is insoluble in the solid state and where the other substances or element or elements behave more nobly in the electrochemical sense to the active element can be formed as a single layer actively antimicrobial surface, because the active element can be brought into solution through galvanic action of biological fluid directly on the alloy mass.

By building on the substrate a plurality of layers of a selected active element or metal, in combination with layers of an element metal or alloy more noble in the electrochemical scale than the selective active element, galvanic action is produced in the presence of biological fluids causing release of ions of the active element. For example, silver may be used as the element for building a first layer and then the nobler gold or platinum may be used for the adjacent layer, etc. The preferred nobler elements are selected from the group consisting of platinum, osmium, iridium, palladium, gold, silver and carbon. Since the layers are in contact with one another, electrons readily flow between them, such that, when the layers are in contact with body or biological fluids which carry various salts, galvanic action is set up as miniature or microscopic galvanic cells to release silver ions. Excellent effects can be accomplished for example by using copper in combination with silver, copper in combination with a copper silver alloy, or copper in combination with gold or a silver copper alloy in combination with gold.

The selection of elements determines the ions to be released.

In one preferred embodiment, a thin film structure is realized that releases for example, gold, silver and/or copper for broad spectrum antimicrobial protection. The remaining elements of the preferred active elements group recited earlier are also very effective.

As in the special case for single layer alloys, with the absence of solid solubility of at least one element of interest discussed above, the thin film morphologies here described for a nominal film surface area, produce a relatively very large, exposed area of contact between dissimilar elements. This results in an enhanced level of release of elements, due to the creation of plurality of microscopic cells through which enhanced ion release by galvanic action is achieved. The importance of the exposed area of contact of the layer materials in an actively antimicrobial surface film is emphasized since simply having adjacent layers of the appropriate elements with their interfaces buried below the surface, does not produce generally (except in the case of a single layer alloy) enhanced antimicrobial activity.

Thin or micro-layers of elements can be laid down on a substance by conventional sputtering vapourization, electrochemical multilayer deposition or sol gel techniques. Many of the various thin film deposition techniques, as described in the monograph "Deposition Technologies for Films and Coatings", by R. F. Bunshah, *Noyes Publications*. 1982, can be used to fabricate specifically metallic multilayer films. These include electrochemical and vacuum deposition methods. In the former, the required structures can be realized either by alternate deposition from two separate electrolytic baths, as described by L. M. Goldman, B. Blanpain and F. Spaepan, *J. Appln. Phys.* 60, 1374 (1986), or by pulsed electroplating from a single bath containing ions of the two metals of interest, as described in U.S. Pat. No. 4,652,348 to J. Yahalom and O. Zadok.

Among the vacuum techniques, the preferred processes are sputtering and evaporation, the latter using resistive, induction or electron-beam heating, since these are most suited to the high rate, large area deposition of metallic films of excellent quality. Multilayers can be realized in a batch process, appropriate for coating discrete substrates individually, wherein the article to be coated rotates or oscillates under two target sources of the elements of interest to be deposited that are shielded from one another so that the article alternately intercepts the vapour stream from one and then the other. Continuous multilayer coating can be realized in a coil to coil operation suitable for flexible substrates, by having the substrate web translate past an array of pairs or series of sources of the elements. Many such systems are in use, primarily for the deposition onto plastic of solar control films, comprising several layers of different materials, the plastic then being laminated to architectural glass. Metallic multilayer films, with individual layer thicknesses in the range of one to a few hundred nanometres (10 A to 1000 A) have been the subject of much recent study due to the variety of interesting mechanical, electronic, and magnetic properties they exhibit for certain metal combinations, including noble metal couples of interest here, as tabulated in Chapter 2 by D. B. McWhan of the monograph "Synthetic Modulated Structures", edited by Chang and Giessen, *Academic Press*, 1985.

Similarly, ionic sputtering may be used to lay down single elements or a plurality (where two or more definite sources are used). The microlayers, as developed on the substrate, can have a thickness of a few molecules and hence be in the range of 5 to 500 nanometres in thickness. Preferred, however, is a total film thickness of about 1 u consisting, say, of ten layers each of about 1000 A thick. The layers are deposited on the surface of the substrate which is to be in contact with the area to be treated; i.e., on a bandage, the layers are applied to the interior surface of the bandage such that when the bandage is applied, the flexible layered film is in contact directly with the body fluids. Since the film is porous the absorbant qualities of the underlying substrate are retained. The substrate need not be flexible however and film may also be deposited on field surfaces, such as catheters and implants.

A textured or open film composition can be created in a variety of ways. In a preferred embodiment, where the substrate itself has a rough surface, for example a latex, the layers may be deposited by direct sputtering; that is, substantially at 90° to the surface. Since portions of the rough surface are in effect at an oblique angle to the sputtering beam, irregularities in the deposited surface are created.

When a smooth substrate is used, oblique angle sputtering of the microlayers will result in a suitably textured surface.

Surface structures produced by metal sputtering on rough surfaces and by oblique angle sputtering are described in *Current Topics in Materials Science*, (1980), Vol. 6, pp. 311–434, by Leamy et al. "The Microstructure of Vapor Deposited Thin Layers" and in *Applied Optics*, Vol. 23, No. 21, Nov. 1, 1984, pp. 3806–3816 by Guenther "Microstructure of Vapor Deposited Optical Coatings".

These references disclose that surfaces so produced have irregularities which give rise to nodules which grow within the metal laminates. Multiple layers thus become exposed at the surface at these nodules. This multiple exposure of metal interfaces provides for high reactivity of the layered textured film compositions and high antimicrobial efficacy.

Texturing may also be created by etching after deposition of the appropriate multilayers of the film.

The texturing of the surface to form a multitude of exposed microlayer interfaces can be generated by a variety of techniques. These include ion beam etching, back sputter etching, chemical etching and mechanical treatment, including, micro abrading, surface cracking by bending, flexing, ultrasonic treatment, expansion of the substrate surface such as by "ballooning" of the article concerned, etc. One preferred method, which produces features on the submicron scale needed, yields uniform texture over large areas, and can be precisely controlled is argon ion beam etching. The development of pronounced texture on materials subjected to ion beam bombardment has been studied extensively, as described in the review article by O. Auciello, *J. Vac. Sci. Tech.* 19, 841 (1982). Different textures are observed on different materials and these depend also on the parameters of the ion beam used. The mechanism for the induced texture is based on microscopic inhomogeneities, either chemical or microstructural, that are present in the material being etched. As the surface is eroded by sputtering under the action of the ion beam, such regions that may have lower sputtering yield than the surrounding matrix, act as a mask which causes the area around them to recede at a relatively higher rate. Once this localized preferential erosion is initiated, the resulting non-eroded structures act further to shadow the surrounding regions and so the texture becomes more accentuated as sputtering continues. The argon ions may be supplied from a glow discharge plasma created above the item being etched, which is biased electrically negative so that the positive argon ions are accelerated to it. Alternatively, the argon ions may be generated by broad beam ion sources which have recently become available commercially. The inhomogeneities in the material to be textured can be intrinsic such as impurities and defects. Impurities may also be supplied externally during etching as in the known process of seeded texturing wherein a particular seed material, such as tantalum, is ion deposited at a low rate onto the specimen simultaneously with the sputter etching of the specimen by the ion beam. In the thin film to be etched, an inhomogeneous microstructure can be created in the material during deposition providing both chemical and microstructural modulation. The resulting texture and composition of the etched film is then, in general, dependent on the particular materials in combination and the structure of the layers. Specific textures have been found in such sputtered multilayer films of Ag and Cu as described by M. Tanemura and F. Okuyama in *J. Vac. Sci. Tech.* A4 (1986). These were studied by them in conjunction with the difficulties that arise from the induced texture in analysing the multilayer films with ion-based spectroscopic techniques. No consideration, however, was given to potential uses of the texture for its own sake.

Specific embodiments of the invention will now be described with reference to the accompanying drawings.

BEST MODES FOR CARRYING OUT THE INVENTION

Figure 1A:
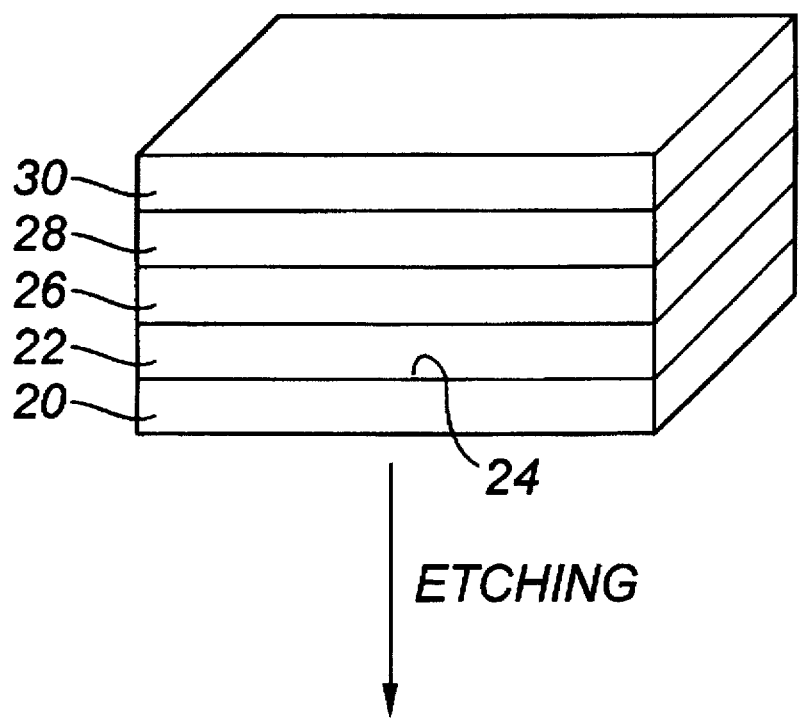
FIG. 1a is a diagrammatic cross sectional representation of a substrate carrying an actively antimicrobial surface of alternate thin layers.
Figure 1B:
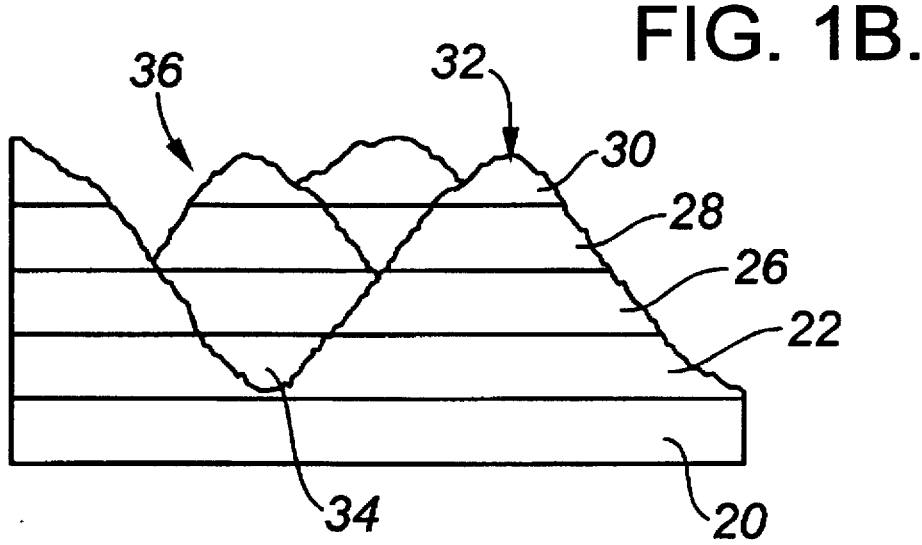
FIG. 1b is an enlarged and enhanced section through the layers of FIG. 1a showing the peaks and valleys of an ion etched surface.

FIGS. 1a and 1b illustrate a substrate 20 of material suitable for biological use and which has formed on it several thin layers containing a selected active element alternating with layers containing a nobler element. In this embodiment, a first microlayer 22 comprising either the active element or the nobler element is deposited directly on the contact or outer surface 24 of the substrate. A second microlayer 26 comprising the other element is deposited on the layer 22. Another layer 28 of the same composition as layer 22 is deposited on the layer 26 and a next layer 30 is deposited on the layer 28. Though omitted for clarity, further alternated layers continue to be added. Typically, there would be a total of about ten layers each about 1000 A thick to give a total film thickness of about 1 um. Each layer is deposited in accordance with standard thin film deposition techniques. To provide a textured surface, the developed layered film of FIG. 1a can then be etched, such as for instance by ion etching in accordance with standard techniques to produce in section an arrangement as shown in FIG. 1b where several peaks 32 and valleys 34 are formed in the surface and expose layers throughout the film 36. The multiple layers, when exposed on the substrate to body fluids, for example in a wound, provide for release of ions of both elements by galvanic solution of the active element and by non-galvanic solution of the nobler element into the wound area. It is apparent that depending on the make-up of each layer, the corresponding biologically significant elements ions will be released. Each alternate layer need not be of a single respective element or metal but may be an alloy of two or more elements (each alloy will express a particular electro chemical position with respect to another alloy). If the film is made up of a single alloy without layering, in which at least one of the elements of interest is insoluble in solid solution, this will release ions without the need for a separate nobler element to be present, the alloy providing the required elements in a form directly accessible to electrolytic solution.

Other methods of texturing the film surface can be used as heretofore described, such as mechanical working, chemical etching, etc. Each mechanism will produce a characteristic break up of the several layers, however, the principal object in such texturing is to expose the lower layers of the film to biological fluid that will contact the upper surface of the film so that the electrochemical action described can take place more readily.

Figure 2A:
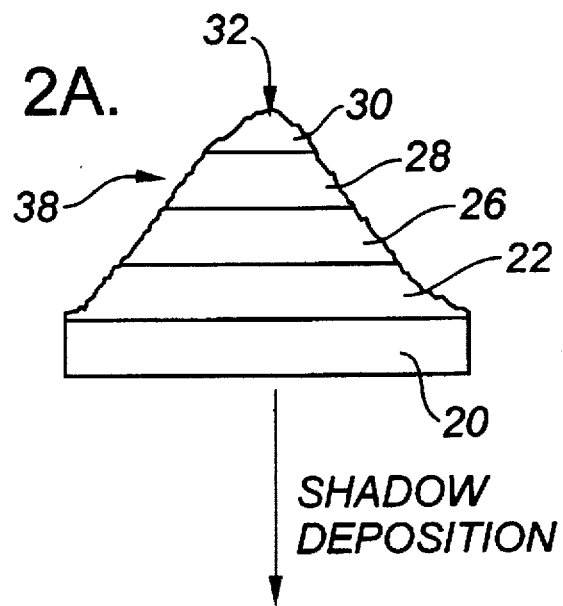
FIG. 2a is a schematic representation in section of a single peak of the etched surface of FIG. 1b.
Figure 2B:
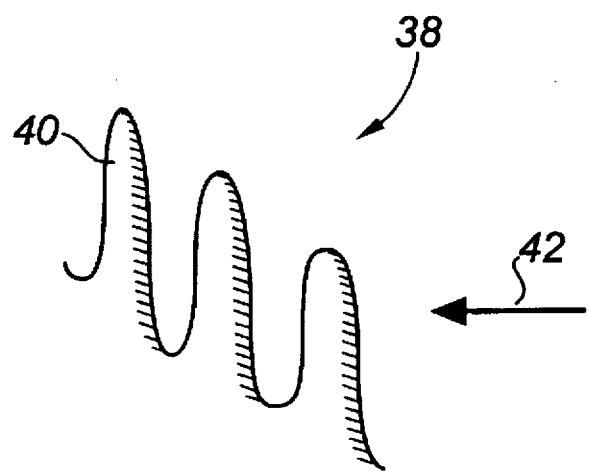
FIG. 2b is an enlarged view of the spicules of FIG. 1b after shadow cast sputtering of a nobler element on the spicule surface.
Figure 2C:
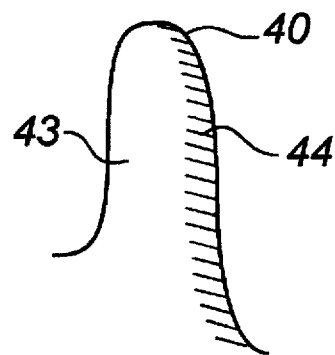
FIG. 2c is a further enlarged view of a single spicule of FIG. 2b showing the relationship of the elements in the release of the active element ions.

FIG. 2 demonstrates a further development of the textured surface of the antimicrobial system. FIG. 2a shows one of the peaks 32 of the active surface 36 of the layered system after etching of FIG. 1b. On the surface of each peak 32 is a jagged edge generally designated 38 to indicate a plurality of spicules projecting upwardly of the surface. In FIG. 1b, the spicules 40 of the jagged surface 38 are shown in enlarged form. By the technique of shadow deposition, a suitable nobler element as gold or platinum can be directed in the direction of arrow 42 to deposit on one side of the spicules. The spicule constitution will depend upon the layer shown. On the right-hand side of each spicule, a desired nobler metal, say platinum or gold, is deposited. As shown in more detail on FIGs. 2b and 2c, an individual spicule 40 of peak 32 has a base 43 of, say silver, copper or silver copper alloy, coated on one side with the more noble element layer 44. Such an individual spicule thus, when exposed to body fluids, sets up an individual microscopic galvanic cell in the region of that spicule to release a continuous supply of the ions of the element or all of the elements in the spicule which are less noble than the element 44. This results in an enhanced metal ion release. Gold may for instance be selected as the more noble element to provide for the galvanic release of the copper or silver ions. However, when gold is desired as the active element ion to be released from a layer, the more noble metal may be platinum. Ions, as well as atoms of the more noble metal, are evidently also released by non-galvanic action. If the microlayers of FIG. 1b are alloys of active elements (for instance silver and copper) both Ag and Cu metal ions are released by galvanic action by the arrangement of FIG. 2b or 2c when the more noble element is gold.

The partial coating of a textured surface by oblique sputtering of a different material, to create surface chemical inhomogeneities does not appear to have been exploited elsewhere. The technique of shadow deposition is a conventional one used in the preparation of specimens for transmission electron microscopy to examine the surface topography of a sample. A thin polymeric replica of the surface is produced which is then shadowed by oblique deposition of a thin film, typically of Pt, to create a contrast effect when the replica is viewed in the microscope. The technique is described in Chapter 3 of "Practical Methods in Electron Microscopy", Volume 8, by J. H. M. Willison and A. J. Rower, North Holland Publishing Co., 1980. This demonstrates the ability to coat surfaces controllably having the fine texture of interest here described without overcoating the whole surface and covering over the desired metal interfaces. This may be readily accomplished in production roll coating, for example, by appropriate choice of source position relative to the moving web and the use of slits to define the coated area.

The actively antimicrobial surface film made up of the textured layers of elements provide for enhanced release of ions of both active element and nobler element, as well as atoms of the nobler element to provide antimicrobial action. If other biologically desirable elements or compounds are included in the active element layer they also will be released. Although the preferred embodiments of the invention have been described with respect to surgical dressings, bandages and the like, the same principles may be applied to other types of surfaces used in microbial treatments, such as water purification and killing of microorganisms in various fluids such as blood. By the technique of texturing, a far more active antimicrobial surface is provided than has been accomplished in other forms of known uses of surface metals in surgical dressings and the like, including those in which macro-galvanic action has been implicated.

The significance of surface texturing of the element microlaminates in producing enhanced release of metal ions, and hence antimicrobial efficacy, is seen from the results in Tables I and IV.

Antimicrobial effects were determined as zones of inhibition measured as in Example I.

EXAMPLE I

Petri plates of agar mixture were prepared according to the manufacturer's (Gibco) instructions, using 1.5% Eagles medium, agar and serum being added to the medium at 50° C. Agar plates were allowed to surface dry for 24 hours. The desired organism, e.g. *S. aureus* ATCC No. 25923 in TSB (Trypticase Soy Broth Difco) was incubated at 37° C. for 16 hours then 1 ml transferred to 10 ml TSB for 16 hours; 0.1 ml aliquots of culture dispensed per petri plate and spread to provide bacterial lawn.

The material or disc to be tested was placed on surface of agar, the plates were incubated at 37° C. for 24 hours and the zone of inhibition measured and corrected zones of inhibition calculated.

The data shown in Tables I and II were obtained as in Example I. Table III experiment with various organisms was similarly conducted.

The data of Table IV were obtained as in Example II.

EXAMPLE II

EXAMPLE II

Sterile synthetic urine was prepared as in Nickel et al, *Eur. J. Clin. Microbiol.*, Vol. 4, #2, pp. 213–218. Discs (coated surfaces or controls) were immersed in synthetic urine at 37° C. for various time periods.

Discs were removed from the urine, washed with sterile deionized water and placed on bacterial lawns prepared as in Example I.

Antimicrobial activity was determined as in Example I.

TABLE I

Effect of Various Surface Treatments on Growth of *Staphylococcus aureus*

| Sample | Corrected Zone of Inhibition* (mm) |
|---|---|
| Ag foil | <1 |
| Ag wire mesh | 2.5 |
| Ag on glass covered 50% with Pt 1 mm bands | <1 |
| Ag bands and Pt bands | 0 |
| Ag 2000 A layers on 1000 A Pt on silicone rubber tubing | 5 |
| Ag 2000 A layers on 1000 A Pt on silicone rubber tubing | 4 |
| Ag 200 A layers on 1000 A Pt on glass tubing | 4 |

*Corrected zone of inhibition = Total zone of inhibiton - diameter of antimicrobial disc

TABLE II

Effect of Textured Films on Various Organisms

| Sample | Texturing | Corrected Zone of Inhibition* (mm) |
|---|---|---|
| 1a Ag on glass, 3000 A | — | <1 |
| 1b Ag on glass, 3000 A | sputter etch | <1 |
| 2a Cu on glass, 3000 A | — | 4.5 |
| 2b Cu on glass, 3000 A | sputter etch | 4.0 |
| 3a 500 A Cu + 500 A Ag layers on glass (10,000 A total) | — | <1 |
| 3b 500 A Cu + 500 A Ag layers on stainless steel (10,000 A total) | sputter etch | 10 |
| 4a 500 A Cu + 500 A Ag layers on stainless steel | — | 3 |
| 4b 500 A Cu + 500 A Ag layers on stainless steel (10,000 A total) | sputter etch | 14 |
| 5a 500 A Cu + 500 A Ag layers on PTFE (Teflon) | — | 3 |
| 5b 500 A Cu + 500 A Ag layers on PTFE (Teflon) (10,000 A total) | — | 13 |
| 6a 500 A Cu + 500 A Ag layers on latex sheet | — | 11 |
| 6b 500 A Cu + 500 A Ag layers on latex sheet | sputter etch | 16 |
| 7a 50 A Cu + 50 A Ag layers on glass (10,000 A total) | — | 1 |

TABLE III

Effect of Textured Films on Various Organisms

| | Corrected Zone of Inhibition** (mm) on: | | |
|---|---|---|---|
| Organism | 50 A Cu and 50 A Ag* on latex, not etched | 500 A Cu and 500 A Ag* on PTFE, sputter etched | 500 A Cu and 500 A Ag* on stainless steel sputter etched |
| *Staphyloccus aureus* | 13 | 13 | 14 |
| *Proteus mirabilis* | 13 | 19 | 18 |
| *Escherichia coli* | 1 | 8 | 12 |

*Total thickness was 10,000 A or 1 μm
**Corrected zone of inhibition = Total zone of inhibition - diameter of antimicrobial disc

TABLE IV

Antimicrobial Effect of Textured Films
After Prolonged Exposure to Synthetic Urine

| Days in Synthetic Urine | 50 A Cu and 50 A Ag on glass 4 min. etch | 50 A Cu and 50 A Ag on latex 4 min. etch |
|---|---|---|
| 0 | 13 | 7 |
| .5 | 13 |  |
| 1 | 13 | 7 |
| 2 | 13 | 8 |
| 3 | 7 | 8 |
| 4 | 7 | 8 |
| 5 | 5 | 8 |

*Corrected zone of inhibition = Total zone of inhibition - diameter of antimicrobial disc
All experiments were done with *Staphylococcus aureus*
All were done in synthetic urine, 37° C.

Table I demonstrates the antimicrobial activity of various film surfaces of types comparable to those previously described. A smooth surface of silver alone, as in silver foil, shows no antimicrobial activity. Slight activity is seen when silver wire mesh is tested. The third system of Table I, which would be expected to produce macro-galvanic action at the limited interfaces between the silver and platinum layers, shows no antimicrobial activity. The last three examples of Table I involve smooth metal layers within the range of thicknesses described in European Patent Application No. 0206204, and show only modest antimicrobial activity.

Table II shows the importance of the opening up or texturing of the film microlayers in producing the enhanced antimicrobial efficacy.

Table II shows seven microlayer laminates of silver, copper or alternating layers of silver and copper and compares the antimicrobial activity of these microlaminates with and without texturing. In each case, the untextured microlaminate (a) is not effective as an antimicrobial surface while texturing of the microlaminate, (b) provides a surface having high antimicrobial efficacy.

Table III shows the antimicrobial effect of the textured composition on further bacterial species.

Table IV shows the antimicrobial activity of the textured films after up to five days of exposure to synthetic urine, and shows the persistence of the antimicrobial activity.

Although preferred embodiments of the invention have been described herein in detail, it will be understood by those skilled in the art that variations may be made thereto without departing from the spirit of the invention or the scope of the appended claims.

Industrial Applicability

Medical devices and apparatus such as catheters, implants, bandages, diapers, diaper liners, dressings and the like can thus be provided with surfaces which are actively antimicrobial when in contact with body fluids so as to release ions which inhibit growth of or kill various types of microorganisms.

We claim:

1. On a substrate for use with biological fluids, an actively antimicrobial surface film, comprising:

at least a pair of superimposed layers on the substrate, the layers of each pair being in electrical contact with each other, one of the layers in each pair being formed from a first element, the other of the layers in each pair being formed from a second element different from the first element, the second element being electrochemically nobler than the first element, at least the first element being an antimicrobially active metal element, each of the layers not in contact with the substrate being substantially discontinuous such that the layer below is exposed, whereby the first element releases ions of the antimicrobially active metal element when a biological fluid is brought into contact with the actively antimicrobial surface film.

2. The actively antimicrobial surface film as defined in claim 1, wherein the antimicrobially active metal element is one or more of platinum, gold, silver, zinc, tin, antimony and bismuth.

3. The actively antimicrobial surface film as defined in claim 2, wherein the second element is electrochemically nobler than the first element and is one or more of platinum, osmium, iridium, palladium, gold, silver and carbon.

4. The actively antimicrobial surface film as defined in claim 1, wherein at least one of the layers in each pair is formed from a metal alloy.

5. The actively antimicrobial surface film as defined in claim 1, which comprises at least two pairs of the layers formed from alternating layers of the first and second elements.

6. The actively antimicrobial surface film as defined in claim 1, wherein one of the layers in each pair is formed from copper, silver and iodine.

7. The actively antimicrobial surface film as defined in claim 5, wherein one of the layers in each pair is formed from copper, silver and iodine.

8. The actively antimicrobial surface film as defined in claim 5, wherein the layers in each pair have a thickness of about 1000 A.

9. The actively antimicrobial surface film as defined in claim 1, wherein the layers form a plurality of spicules, each spicule being formed from alternating layers of the first and second elements, each of the layers being in contact with the layer on which it is superimposed.

10. The actively antimicrobial surface film as defined in claim 5, wherein the layers form a plurality of spicules, each spicule being formed from alternating layers of the first and second elements, each of the layers being in contact with the layer on which it is superimposed.

11. The actively antimicrobial surface film as defined in claim 9, which further comprises a partial coating on the spicules, the partial coating being formed by shadow deposition from a third element which is electrochemically nobler than the first and second elements.

12. The actively antimicrobial surface film as defined in claim 1, wherein the discontinuity in the layers not in contact with the substrate is formed by texturing the layers.

13. The actively antimicrobial surface film as defined in claim 5, wherein the discontinuity in the layer of each pair most distant from the substrate is formed by texturing the layer.

14. A process for the production of an actively antimicrobial surface film on a substrate for use with electrolytes containing biological fluids, comprising the steps of:

forming a first layer comprising one of a first element or a second element on a surface of the substrate;

forming a second layer on the first layer, comprising the other of the first element or the second element of the first layer; and texturing at least the second layer to expose the first layer;

wherein at least the first element is an antimicrobially active metal element, the second element being different from, and electrochemically nobler than the first element, and the first and second elements in the first and second layers being in electrical contact with each other, and whereby when a biological fluid is brought into contact with the actively antimicrobial surface film, both the first and second layers are contacted and the first element releases ions of the antimicrobially active metal element.

15. The process as defined in claim 14, which includes the further steps of forming alternating additional layers of the first and second elements, and texturing each of the layers not in contact with the substrate such that the layer below is exposed.

16. The process as defined in claim 15, wherein the film has a total thickness of about 1μ and each of the first and second layers have thicknesses of about 1000 A.

17. The process as defined in claim 14, wherein the first and second layers are formed by vapor deposition.

18. The process as defined in claim 14, wherein the first and second layers are formed by chemical deposition.

19. The process as defined in claim 14, wherein the first and second layers are formed by ionic deposition.

20. The process as defined in claim 14, wherein first and second layers are textured by etching.

21. The process as defined in claim 14, wherein the antimicrobially active metal element is one or more of platinum, gold, silver, copper, zinc, tin, antimony, and bismuth, and the second element is electrochemically nobler than the antimicrobially active metal element and comprises of platinum, osmium, iridium, palladium, gold, silver and carbon.

* * * * *